United States Patent [19]
Kennis et al.

[11] Patent Number: 6,156,757
[45] Date of Patent: Dec. 5, 2000

[54] 1,2,3,4-TETRAHYDRO-BENZOFURO[3,2-C] PYRIDINE DERIVATIVES

[75] Inventors: Ludo Edmond Josephine Kennis, Turnhout; Christopher John Love, Deurne; Paul François Bischoff, Berchem, all of Belgium

[73] Assignee: Janssen Pharmaceutica N.V., Belgium

[21] Appl. No.: 09/402,593

[22] PCT Filed: Apr. 2, 1998

[86] PCT No.: PCT/EP98/02136

§ 371 Date: Oct. 4, 1999

§ 102(e) Date: Oct. 4, 1999

[87] PCT Pub. No.: WO98/45297

PCT Pub. Date: Oct. 15, 1998

[30] Foreign Application Priority Data

Apr. 8, 1997 [EP] European Pat. Off. .............. 97201045

[51] Int. Cl.[7] ..................... C07D 491/04; C07D 498/04; C07D 513/04; A61K 31/435
[52] U.S. Cl. ............................ 514/258; 546/89; 544/278; 544/281; 544/282; 544/268; 544/331; 544/250; 514/267; 514/265; 514/274; 514/291
[58] Field of Search ..................................... 544/278, 282, 544/281, 331, 268, 250; 514/267, 265, 274, 258, 291; 546/89

[56] References Cited

U.S. PATENT DOCUMENTS 4,661,498 4/1987 Wick et al. ............................ 514/302

FOREIGN PATENT DOCUMENTS

| | | |
|---|---|---|
| 0 178 201 | 4/1986 | European Pat. Off. . |
| 0 214 556 | 3/1987 | European Pat. Off. . |
| 0 339 959 | 11/1989 | European Pat. Off. . |
| 0339959 | 11/1989 | European Pat. Off. . |

OTHER PUBLICATIONS

Printout for Aksanova et al. Khim.–Farm. Zh. (1975), 9, 7–9, 1975.

*Primary Examiner*—Mukund J. Shah
*Assistant Examiner*—Hong Liu
*Attorney, Agent, or Firm*—Mary Appollina

[57] ABSTRACT

The present invention concerns the compounds of formula

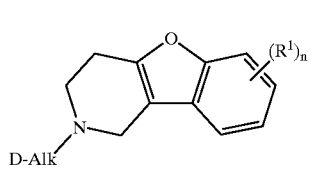

(I)

the N-oxides, the pharmaceutically acceptable addition salts and the stereochemically isomeric forms thereof, wherein each $R^1$ is independently hydrogen, halogen, $C_{1-6}$alkyl, nitro, hydroxy or $C_{1-4}$alkyloxy; Alk is $C_{1-6}$alkanediyl; n is 1 or 2; D is an optionally substituted mono-, bi- or tricyclic nitrogen containing heterocycle having central $\alpha_2$-adrenoceptor antagonist activity. It further relates to their preparation, compositions comprising them and their use as a medicine.

10 Claims, No Drawings

1,2,3,4-TETRAHYDRO-BENZOFURO[3,2-C] PYRIDINE DERIVATIVES

CROSS REFERENCE TO RELATED APPLICATIONS

This application is a National Stage application under 35 U.S.C. 371 of PCT/EP98/02136 filed Apr. 2, 1998, which claims priority from EP 97.201.045.8, filed Apr. 8, 1997.

The present invention concerns 1,2,3,4-tetrahydro-benzofuro[3,2-c]pyridine derivatives having central $\alpha_2$-adrenoceptor antagonist activity. It further relates to their preparation, compositions comprising them and their use as a medicine. Central $\alpha_2$-adrenoceptor antagonists are known to increase noradrenaline release by blocking presynaptic $\alpha_2$-receptors which exert an inhibiting control over the release of the neurotransmitter. By increasing the noradrenaline concentrations, $\alpha_2$-antagonists can be used clinically for the treatment or prophylaxis of depression, cognitive disturbances, Parkinson's disease, diabetes mellitus, sexual dysfunction and impotence, elevated intraocular pressure, and diseases related to disturbed enterokinesia, since all these conditions are associated with a deficiency of noradrenaline in the central or peripheral nervous system.

The compounds of the present invention are novel and have a specific and selective binding affinity for the different known subtypes of the $\alpha_2$-adrenoceptors, i.e. the $\alpha_{2A}$, $\alpha_{2B}$ and $\alpha_{2C}$-adrenoceptor.

The present invention concerns the compounds of formula

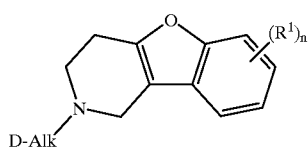

(I)

the N-oxide forms, the pharmaceutically acceptable addition salts and the stereochemically isomeric forms thereof, wherein:

each $R^1$ is independently hydrogen, halogen, $C_{1-6}$alkyl, nitro, hydroxy or $C_{1-4}$alkyloxy;

Alk is $C_{-6}$alkanediyl;

n is 1 or 2;

D is 1- or 2-benzimidazolyl, 2(3H)benzoxazolone-3-yl or a radical of formula

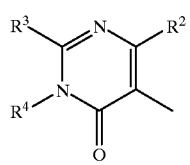

(a)

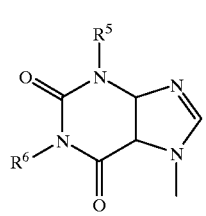

(b)

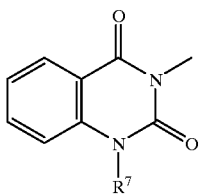

(c)

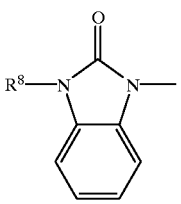

(d)

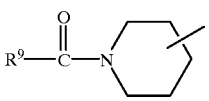

(e)

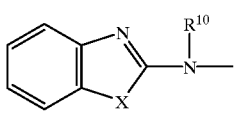

(f)

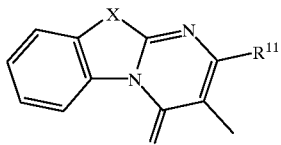

(g)

wherein
each X independently represents O, S or $NR^{12}$;
$R^2$ is hydrogen, $C_{1-6}$alkyl, aryl or aryl $C_{1-6}$alkyl;
$R^3$ is hydrogen, $C_{1-6}$alkyl, $C_{1-6}$alkyloxy, $C_{1-6}$alkylthio, amino or mono- or di($C_{1-6}$alkyl)amino;
$R^4$, $R^5$, $R^6$, $R^7$, $R^8$, $R^{10}$, $R^{11}$ and $R^{12}$ each independently are hydrogen or $C_{1-6}$alky
$R^9$ is hydrogen, $C_{1-6}$alkyl or aryl; or
$R^3$ and $R^4$ taken together may form a bivalent radical —$R^3$—$R^4$— of formula

| | |
|---|---|
| —$CH_2$—$CH_2$—$CH_2$— | (a-1); |
| —$CH_2$—$CH_2$—$CH_2$—$CH_2$— | (a-2); |
| —CH=CH—$CH_2$— | (a-3); |
| —$CH_2$—CH=CH— | (a-4) | or

| | |
|---|---|
| —CH=CH—CH=CH— | (a-5); | wherein one or two hydrogen atoms of said radicals (a-1) to (a-5) each independently may be replaced by halo, $C_{1-6}$alkyl, aryl$C_{1-6}$alkyl, trifluoromethyl, amino, hydroxy, $C_{1-6}$alkyloxy or $C_{1-10}$alkylcarbonyloxy; or where possible, two geminal hydrogen atoms may be replaced by $C_{1-6}$alkylidene or aryl$C_{1-6}$alkylidene; or
—$R^3$—$R^4$— may also be

| | |
|---|---|
| —S—$CH_2$—$CH_2$— | (a-6); |

—S—CH$_2$—CH$_2$—CH$_2$— (a-7);

—S—CH=CH— (a-8);

—NH—CH$_2$—CH$_2$— (a-9);

—NH—CH$_2$—CH$_2$—CH$_2$— (a-10);

—NH—CH=CH— (a-11);

—NH—CH=N— (a-12);

—S—CH=N— (a-13);

or

—CH=CH—O— (a-14);

wherein one or where possible two or three hydrogen atoms in said radicals (a-6) to (a-14) each independently may be replaced by C$_{1-6}$alkyl or aryl; and aryl is phenyl or phenyl substituted with halo or C$_{1-6}$alkyl.

As used in the foregoing definitions the term halogen is generic to fluoro, chloro, romo and iodo. The term C$_{1-6}$alkyl defines straight and branched saturated hydrocarbons, having from 1 to 6 carbon atoms such as, for example, methyl, ethyl, propyl, butyl, 1-methylethyl, 1,1-dimethylethyl, 2-methylpropyl, pentyl, hexyl and the like. The term C$_{1-10}$alkyl is meant to include C$_{1-6}$alkyl radicals and the higher homologues thereof having 7 to 10 carbon atoms such as, for example, heptyl, octyl, nonyl, decyl and the like. The term C$_{1-6}$alkanediyl defines bivalent straight or branch chained alkanediyl radicals having from 1 to 6 carbon atoms such as, for example, methylene, 1,2-ethanediyl, 1,3-propanediyl, 1,4-butanediyl, 1,5-pentanediyl, 1,6-hexanediyl and the like; the term C$_{1-6}$alkylidene defines bivalent straight or branch chained alkylidene radicals having from 1 to 6 carbon atoms such as, for example, methylene, ethylidene, 1-propylidene, 1-butylidene, 1-pentylidene, 1-hexylidene and the like.

The addition salts as mentioned herein are meant to comprise the therapeutically active addition salt forms which the compounds of formula (I) are able to form with appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are also meant to comprise the therapeutically active non-toxic base, in particular, a metal or amine addition salt forms which the compounds of formula (I) are able to form. Said salts can conveniently be obtained by treating the compounds of formula (I) containing acidic hydrogen atoms with appropriate organic and inorganic bases such as, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Conversely said salt forms can be converted by treatment with an appropriate base or acid into the free acid or base form.

The term addition salt as used hereinabove also comprises the solvates which the compounds of formula (I) are able to form and said solvates are meant to be included within the scope of the present invention. Examples of such solvates are, e.g. the hydrates, alcoholates and the like.

The N-oxide forms of the compounds of formula (I) are meant to comprise those compounds of formula (I) wherein one or several nitrogen atoms are oxidized to the so-called N-oxide.

The term stereochemically isomeric forms as used herein defines all the possible isomeric forms in which the compounds of formula (I) may occur. Unless otherwise mentioned or indicated, the chemical designation of compounds denotes the mixture of all possible stereochemically isomeric forms, said mixtures containing all diastereomers and enantiomers of the basic molecular structure.

Some of the compounds of formula (I) may also exist in their tautomeric forms. Such forms although not explicitly indicated in the above formula are intended to be included within the scope of the present invention.

Whenever used hereinafter, the term compounds of formula (I) is meant to include also the N-oxide forms, the pharmaceutically acceptable addition salts and all stereoisomeric forms.

A special group of compounds are those compounds of formula (I) wherein n is 1 and $R^1$ is hydrogen, halogen, C$_{1-6}$alkyl or nitro.

An interesting group of compounds are those compounds of formula (I) wherein n is 1 and $R^1$ is hydrogen, chloro, fluoro, methyl or nitro, more particularly $R^1$ is hydrogen; or, wherein n is 2 and $R^1$ is methoxy Another interesting group of compounds are those compounds of formula (I) wherein Alk is methylene, 1,2-ethanediyl, 1,3-propanediyl, 1,4-butanediyl or 1,5-pentanediyl.

Still another interesting group of compounds are those compounds of formula (I) wherein D is 1-benzimidazolyl; 2(3H)benzoxazolone-3-yl, or D is a radical of formula (a) wherein $R^3$ is C$_{1-6}$alkylthio and $R^4$ is C$_{1-6}$alkyl; or wherein $R^3$ and $R^4$ are taken together to form a bivalent radical of formula (a-2) or (a-5) wherein one or two hydrogen atoms of said radicals each independently may be replaced by halo, C$_{1-6}$alkyl, arylC$_{1-6}$alkyl, trifluoromethyl, amino, hydroxy, C$_{1-6}$alkyloxy or C$_{1-10}$alkylcarbonyloxy; or where possible, two geminal hydrogen atoms may be replaced by C$_{1-6}$alkylidene or arylC$_{1-6}$alkylidene; or a bivalent radical of formula (a-6), (a-7), (a-8), (a-11) or (a-14) wherein one or where possible two or three hydrogen atoms in said radicals each independently may be replaced by C$_{1-6}$alkyl or aryl; or D is a radical of formula (b) wherein $R^5$ and $R^6$ are C$_{1-6}$alkyl; or D is a radical of formula (c) wherein $R^7$ is hydrogen; or D is a radical of formula (d) wherein $R^8$ is hydrogen or C$_{1-6}$alkyl; or D is a radical of formula (e) wherein $R^9$ is aryl; or D is a radical of formula (f) wherein X is S and $R^{10}$ is hydrogen; or D is a radical of formula (g) wherein X is S and $R^{11}$ is C$_{1-6}$alkyl.

Particular compounds are those compounds of formula (I) wherein D is 2(3H)benzoxazolone-3-yl, or D is a radical of formula (a) wherein $R^3$ is methylthio and $R^4$ is methyl; or wherein $R^3$ and $R^4$ are taken together to form a bivalent radical of formula (a-2) or (a-5) wherein one or two hydrogen atoms each independently may be replaced by halo, C$_{1-6}$alkyl, C$_{1-6}$alkyloxy, arylC$_{1-6}$alkyl, trifluoromethyl, amino or hydroxy, or wherein two geminal hydrogen atoms are replaced by arylC$_{1-6}$alkylidene; or $R^3$ and $R^4$ are taken together to form a bivalent radical of formula (a-6), (a-7), (a-8), (a-11) or (a-14) wherein one or where possible two or three hydrogen atoms are replaced by C$_{1-6}$alkyl; or D is a radical of formula (b) wherein $R^5$ and $R^6$ are methyl; or D is a radical of formula (c) wherein $R^7$ is hydrogen; or D is a radical of formula (d) wherein $R^8$ is hydrogen; or D is a radical of formula (e) wherein $R^9$ is aryl connected to Alk in the 4 position of the piperidine moiety; or D is a radical of formula (f) wherein X is S and $R^{10}$ is hydrogen; or D is a radical of formula (g) wherein X is S and $R^{11}$ is methyl.

Preferred compounds are those compounds of formula (I) wherein n is 1, $R^1$ is hydrogen and D is a radical of formula (a) wherein $R^3$ and $R^4$ taken together form a bivalent radical of formula (a-2) or (a-5) wherein one or two hydrogen atoms each independently may be replaced by halo, methyl, methoxy, arylmethyl, trifluoromethyl, amino or hydroxy, or wherein two geminal hydrogen atoms are replaced by arylmethylene; or $R^3$ and $R^4$ taken together form a bivalent radical of formula (a-6), (a-7), (a-8), (a-11) or (a-14) wherein one or where possible two or three hydrogen atoms are replaced by methyl.

Most preferred compounds are:
3-[2-[3,4-dihydrobenzofuro[3,2-c]pyridin-2(1H)-yl]ethyl]-2-methyl-4H-pyrido-[1,2-a]pyrimidin-4-one;
6-[[3,4-dihydrobenzofuro[3,2-c]pyridin-2(1H)-yl]ethyl]-7-methyl-5H-thiazolo-[3,2-a]pyrimidin-5-one;
6-[[3,4-dihydrobenzofuro[3,2-c]pyridin-2(1H)-yl]ethyl]-3,7-dimethyl-5H-thiazolo-[3,2-a]pyrimidin-5-one;
3-[2-[3,4-dihydrobenzofuro[3,2-c]pyridin-2(1H)-yl]ethyl]-2,7-dimethyl-4H-pyrido-[1,2-a]pyrimidin-4-one; the N-oxides, the pharmaceutically acceptable addition salts and the stereochemically isomeric forms thereof The compounds of formula (I) can generally be prepared by N-alkylating a 1,2,3,4-tetrahydro-benzofurano[3,2-c]pyridine derivative of formula (II) with an alkylating reagent of formula (III) following the procedure described in EP-A-0,037,265, EP-A-0,070,053, EP-A-0,196,132 and in EP-A-0,378,255.

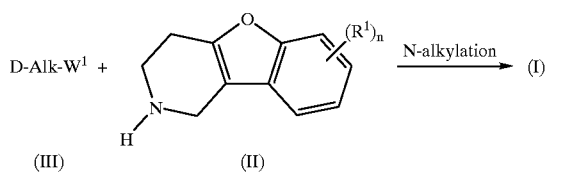

In intermediate (III), $W^1$ represents an appropriate reactive leaving group such as, for example, halo, e.g. chloro, bromo or iodo; sulfonyloxy, e.g. methanesulfonyloxy, 4-methylbenzenesulfonyloxy.

In this and the following reactions, the reaction products may be isolated from the reaction medium and, if necessary, further purified according to methodologies generally known in the art such as extraction, crystallization, trituration and chromatography.

The compounds of formula (I) wherein D is a radical of formula (e), being represented by formula (I-e), may be prepared by deprotecting a N-protected intermediate of formula (IV) wherein P is a protective group such as, for example, a $C_{1-4}$alkyloxycarbonyl group, and subsequently N-acylating the resulting intermediate with an acyl derivative of formula (V) wherein $W^2$ is an appropriate reactive leaving group such as, for example, a halogen.

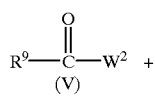

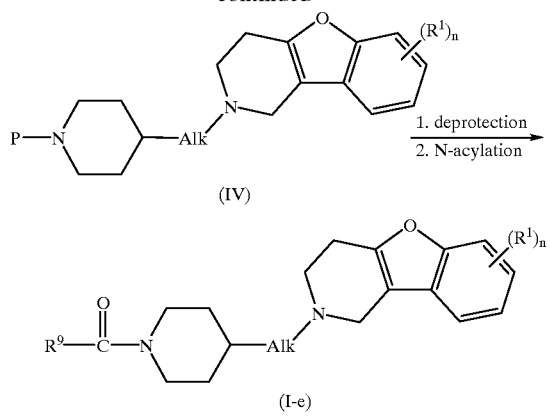

The compounds of formula (I) wherein D is a radical of formula (f), being represented by formula (I-f), can be prepared by N-alkylating an amine of formula (VI) with an intermediate of formula (VII) wherein $W^3$ is an appropriate reactive leaving group such as, for example, a halogen.

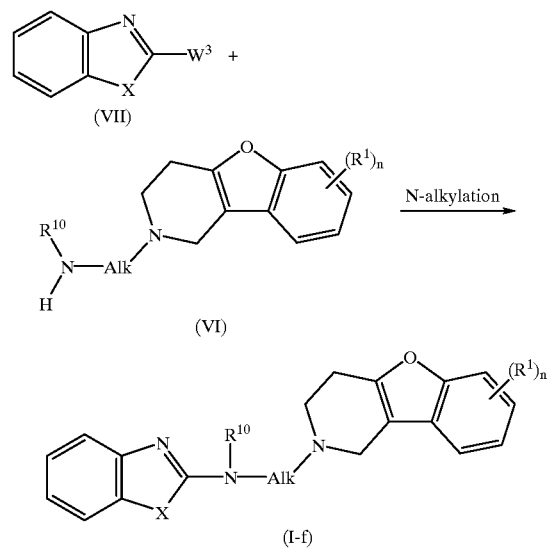

The compounds of formula (I) may be converted into each other following art-known functional group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

A number of intermediates and starting materials are commercially available or are known compounds which may be prepared according to art-known methodologies.

For example, some of the intermediates of formula (III) and their preparations are described in EP-A-0,037,265, EP-A-0,070,053, EP-A-0,196,132 and in EP-A-0,378,255.

Intermediates of formula (II) can be prepared following the procedures described in Cattanach C. et al. (J. Chem. Soc (C), 1971, p53–60); Kartashova T. (Khim. Geterotsikl. Soedin., 1979 (9), p 1178–1180) and Zakusov. V. Et al. (Izobreteniya, 1992 (15), p 247).

A particular synthesis route for the preparation of intermediates of formula (II) is depicted in scheme 1.

Step a can be performed analogous to the procedure described in Heterocycles (1994), 39(1), p. 371–380. Step b can be performed analogous to the procedure described in J. Med. Chem. (1986), 29(9), p. 1643–1650. Further reaction steps can be performed analogous to the ones described in J. Hetercycl. Chem. (1979), 16, p. 1321.

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromato-

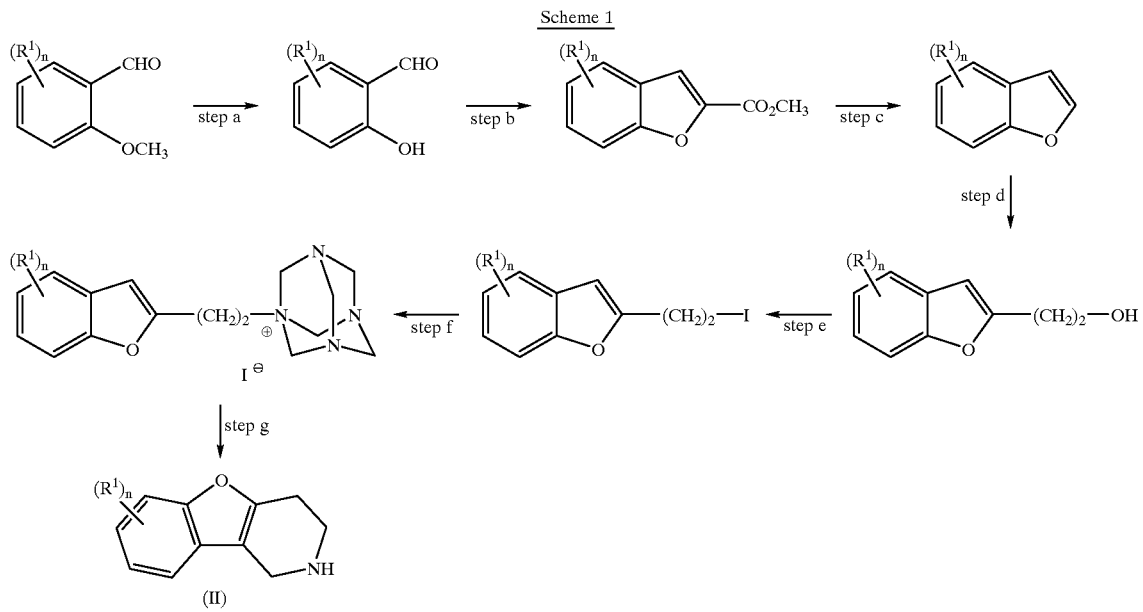

Step a can be performed analogous to the procedure described in tetrahedron (1981), 37, p 979–982. Benzofurans resulting from step c have been used as intermediates in U.S. Pat. No. 4,210,655. The further reaction steps are analogous to the reaction procedures described in U.S. Pat. No. 3,752,820.

Alternatively, intermediates of formula (II) can be prepared using the reaction steps depicted in scheme 2.

graphic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid

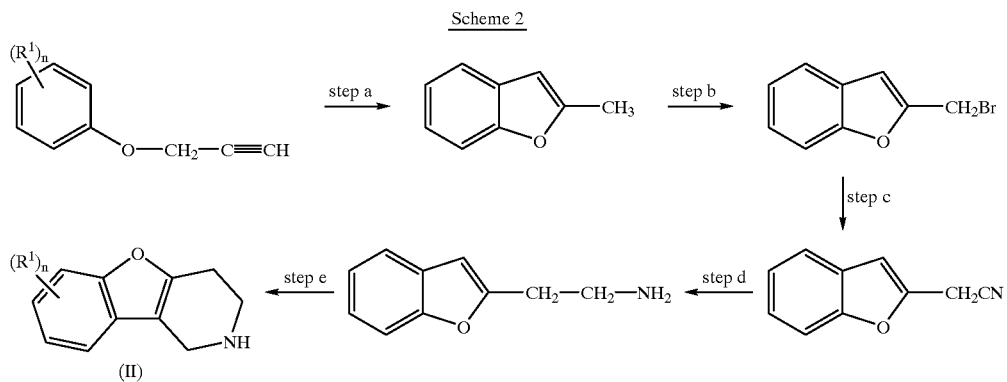

chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereo specifically. The pure and mixed stereochemically isomeric forms of the compounds of formula (I) are intended to be embraced within the scope of the present invention.

The compounds of formula (I), the N-oxides, the pharmaceutically acceptable addition salts and stereochemically isomeric forms thereof, block the presynaptic $\alpha_2$-receptors on central noradrenergic neurons thus increasing the noradrenaline release. Blocking said receptors will suppress or relieve a variety of symptoms associated with a deficiency of noradrenaline in the central or peripheral nervous system. Therapeutic indications for using the present compounds are depression, cognitive disturbances, Parkinson's disease, diabetes mellitus, sexual dysfunction and impotence and elevated intraocular pressure.

Blocking $\alpha_2$ receptors in the central nervous system has also been shown to enhance the release of serotonine which may add to the therapeutic action in depression (Maura et al., 1992, Naunyn-Schmiedeberg's Arch. Pharmacol., 345: 410–416).

It has also been shown that blocking $\alpha_2$ receptors with the present compounds induces an increase of extracellular DOPAC (3,4-dihydro-phenylacetic acid) which is a metabolite of dopamine and noradrenaline.

In view of the usefulness of the subject compounds in the treatment of diseases associated with a deficiency of noradrenaline in the central nervous system, in particular depression and Parkinson's disease, the present invention provides a method of treating warm-blooded animals suffering from such diseases, in particular depression and Parkinson's disease, said method comprising the systemic administration of an therapeutically effective amount of a compound of formula (I) or a pharmaceutically acceptable addition salt thereof.

The present compounds are also potentially useful in the treatment of Alzheimer's disease and dementia as it is known that $\alpha_2$-antagonists promote the release of acetylcholine (Tellez et al. 1997, J. Neurochem. 68:778–785).

In general it is contemplated that an effective therapeutic daily amount would be from about 0.01 mg/kg to about 4 mg/kg body weight.

The present invention thus also relates to compounds of formula (I) as defined hereinabove for use as a medicine. Further, the present invention also relates to the use of a compound of formula (I) for the manufacture of a medicament for treating depression or Parkinson's disease.

Ex vivo as well as in vitro receptor signal-transduction and receptor binding studies, and the ability to reverse a clonidine-induced reduction of electrically-stimulated noradrenaline release from rabbit cerebral cortex can be used to evaluate the $\alpha_2$ adrenoceptor antagonism of the present compounds. As indices of central $\alpha_2$-adrenoceptor blockade in vivo, the reversal of the loss of righting reflex observed in rats after intravenous injection of xylazine and inhibition of the tremors induced by reserpine in rats can be used.

In the social dominance test in which rats have to compete for drinking a sucrose solution, the compounds of the present invention were able to increase the competitive behavior of the submissive rats.

The present compounds also show effects on the intestine; they reverse the antidiarrheal effect of clonidine and stimulate fecal excretion in non-fasted rats. In dogs, they are able to accelerate the onset of $MgSO_4$-induced diarrhea and in a gastric emptying test in dogs, they have the ability of reversing the delay of gastric emptying induced by the $\alpha_2$ agonist lidamidine. The present compounds are therefore also useful for the treatment of diseases related to disturbed enterokinesia.

The compounds of the present invention also have the ability to rapidly penetrate into the central nervous system.

For administration purposes, the subject compounds may be formulated into various pharmaceutical compositions comprising a pharmaceutically acceptable carrier and, as active ingredient, a therapeutically effective amount of a compound of formula (I). To prepare the pharmaceutical compositions of this invention, an effective amount of the particular compound, in addition salt or in free acid or base form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions containing compounds of formula (I) may be formulated in an oil for prolonged action. Appropriate oils for this purpose are, for example, peanut oil, sesame oil, cottonseed oil, corn oil, soy bean oil, synthetic glycerol esters of long chain fatty acids and mixtures of these and other oils. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. Addition salts of (I) due to their increased water solubility over the corresponding free base or free acid form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The following examples are intended to illustrate the present invention.

Experimental Part

Hereinafter, "RT" means room temperature, "THF" means tetrahydrofuran, "DMF" means N,N-dimethylformamide and "DIPE" means diisopropyl ether.

A. Preparation of the Intermediates

EXAMPLE A1

A mixture of O-phenylhydroxylamine hydrochloride (1:1) (0.625 mol) and 4,4-piperidinediol hydrochloride (1:1) (0.682 mol) in 2-propanol (615 ml) was stirred at 20° C. HCl (353 ml) was added dropwise at 20° C. The reaction mixture was gently heated to reflux temperature. The reaction mixture was stirred and refluxed for 3 hours, then cooled to room temperature. The precipitate was filtered off, washed with DIPE, and dried. This fraction was crystallized from water (1600 ml). The desired compound was allowed to crystallize out while stirring. The precipitate was filtered off, washed with 2-propanol and DIPE, then dried, yielding 84 g (64%) of 1,2,3,4-tetrahydrobenzofuro[3,2-c]pyridine hydrochloride (1:1) (interm. 1).

EXAMPLE A2

1,4-dioxa-8-azaspiro[4,5]decane (0.12 mol) was added dropwise to a mixture of O-(4-fluorophenyl)hydroxylamine hydrochloride (1: 1) (0.1 mol) in a mixture of HCl and 1,1-oxybisethane (150 ml). The reaction mixture was stirred and refluxed for 4 hours and then cooled. The precipitate was filtered off and dried, then recrystallized from water, yielding 10 g (43.9%) 1,2,3,4-tetrahydro-8-fluorobenzofuro[3,2-c]pyridine hydrochloride (interm. 2; mp. >300° C.).

EXAMPLE A3 a) 1,2,3,4-tetrahydro-2-methyl-6-nitrobenzofuro[3,2-c] pyridine (0.0224 mol), prepared according to the procedure described in J. Chem. Soc. (C), 1971, p53-60, was dissolved in 1,2-dichloroethane (40 ml), and cooled to 0° C. At this temperature, (1-chloroethyl) acetylchloride (0.0291 mol) was added dropwise. The suspension was stirred and refluxed for 2 hours. 1,2-dichloroethane was evaporated. The mixture was dissolved in methanol, stirred and refluxed for 2 hours, then filtered. Both the filtrate and crystals were treated with 2 N $Na_2CO_3$ and this mixture was extracted with $CH_2Cl_2$. The separated organic layer was dried, filtered, and the solvent evaporated. The residue was purified by column chromatography over silica gel (eluent: $CH_2Cl_2$/ $CH_3OH$ 90/10). The desired fractions were collected and the solvent was evaporated, yielding 1.5 g 1,2,3,4-tetrahydro-6-nitrobenzofuro[3,2-c]-pyridine (interm. 4).

b) A mixture of 1,2,3,4-tetrahydro-2-methyl-6-nitrobenzofuro[3,2-c]pyridine (0.0215 mol) and triethylamine (2 g) in THF (200 ml) was hydrogenated with palladium-on-charcoal catalyst 10% (2 g) as a catalyst in the presence of thiophene 4% (2 ml). After uptake of $H_2$ (3 equivalents), the catalyst was filtered off and the filtrate was evaporated, yielding 4.2 g 1,2,3,4-tetrahydro-6-amino-2-methylbenzofuro[3,2-c]pyridine (interm. 7).

c) A mixture of intermediate (7) (0.0100 mol) in HCl (2 ml) was diazotized at −5° C. with $NaNO_2$ (0.0105 mol) in water (1.2 ml), during 30 minutes. The solution was stirred for 30 minutes at −5° C. A mixture of CuCl (0.010 mol) in HCl (10.6 ml) was added during 10 minutes. The resulting reaction mixture was stirred for 15 minutes at 80° C., then cooled to 20° C. After dilution with water, a 40% $K_2CO_3$ solution was added in excess, and this mixture was extracted with $CH_2Cl_2$. The separated organic layer was dried, filtered, and the solvent evaporated, yielding 1.7 g (78%) 1,2,3,4-tetrahydro-6-chloro-2-methylbenzofuro[3,2-c]-pyridine (interm. 8).

EXAMPLE A4 a) A mixture of intermediate (1) (0.03 mol), chloroacetonitrile (0.04 mol), potassium iodide (0.1 g) and $Na_2CO_3$ (5 g) in 4-methyl-2-pentanone (180 ml) was stirred and refluxed for 3 hours. The mixture was filtered warm and the filtrate was evaporated. The residue was purified over silica gel on a glass filter (eluent: $CH_2Cl_2$/($CH_3OH/NH_3$) 95/5). The desired fractions were collected and the solvent was evaporated. The residue was crystallized from DIPE/ petroleum ether 1/1. The precipitate was filtered off and dried, yielding 5.74 g (90%) of 3,4-dihydrobenzofuro[3,2-c]pyridine-2(1H)-acetonitrile (intern. 10; mp 78° C.).

b) A mixture of intermediate (10) (0.027 mol) in $CH_3OH$/ $NH_3$ (200 ml) was hydrogenated with Raney Nickel (2 g) as a catalyst in the presence of thiophene 4% (1 ml). After uptake of $H_2$ (2 equivalents), the catalyst was filtered over dicalite and the filtrate was evaporated, yielding 5 g (85.6%) 1,2,3,4-tetrahydro-2-(aminoethyl)-benzofuro[3,2-c]pyridine (intern. 12).

EXAMPLE A5 a) A mixture of intermediate (1) (0.03 mol), ethyl (5-chloropentyl)carbamate (0.04 mol), potassium iodide (0.1 g) and $Na_2CO_3$ (5.7 g) in toluene (250 ml) was stirred and refluxed overnight. The reaction mixture was cooled, stirred in water (200 ml), and the layers were separated. The organic phase was evaporated. The residue was purified by column chromatography over silica gel (eluent: $CH_2Cl_2$/ $CH_3OH$ 95/5). The pure fractions were collected and the solvent was evaporated, yielding 7 g of ethyl [5-(3,4-dihydrobenzofuro[3,2-c]pyridin-2(1H)-yl)pentyl]carbamate (interm. 15).

b) A mixture of intermediate (15) (0.021 mol) and potassium hydroxide (12 g) in 2-propanol (120 ml) was stirred and refluxed for 6 hours. The solvent was evaporated. The residue was partitioned between $CH_2Cl_2$ and water. The organic layer was separated, dried, filtered and the solvent was evaporated, yielding 4 g of 3,4-dihydrobenzofuro[3,2-c]pyridine-2(11H)-pentanamine (interim. 16).

EXAMPLE A6 a) A mixture of 3-hydroxymethyl-piperidine (0.6 mol) and $Na_2CO_3$ (130 g) in $CHCl_3$ (600 ml) and water (600 ml) was stirred at 10° C. Ethyl chloroformate (115 g) was added dropwise (temperature was kept at 10° C.). The mixture was stirred until the temperature reached room temperature and the reaction mixture was stirred overnight. Water (500 ml) was added. The organic layer was separated, washed with water, dried, filtered and the solvent was evaporated, yielding 110 g (98%) of (±)-ethyl 3-(hydroxymethyl)-1-piperidinecarboxylate (interm. 17).

b) A solution of methylphenylsulfonylchloride (0.79 mol) in pyridine (200 ml) was added dropwise to a solution of intermediate (17) (0.4 mol) in pyridine (150 ml), stirred at 10° C. The reaction mixture was stirred until the temperature reached room temperature and the reaction mixture was stirred overnight. Under continuous stirring, this mixture was poured out into water (1000 ml) and was extracted with methylisobutyl ketone. The separated organic layer was washed with water, dried, filtered and the solvent was evaporated. The residue was crystallized from a mixture of diisopropylether and petroleum ether. The precipitate was filtered off and dried, yielding 96 g (70.3%) of (±)-ethyl 3-[[[(4-methylphenyl)sulfonyl]oxy]methyl]-1-piperidinecarboxylate (interm. 18).

c) A mixture of intermediate (18) (0.0088 mol), free base of intermediate (1) (0.0080 mol) and $Na_2CO_3$ (0.016 mol) in DMF (25 ml) was stirred and refluxed overnight. The reaction mixture was cooled and the solvent was evaporated. The residue was partitioned between $CH_2Cl_2$ and a 50% aqueous NaCl solution. The layers were separated. The aqueous layer was extracted three times with $CH_2Cl_2$. The combined organic layers were dried, filtered and the solvent evaporated. The residue was purified by HPLC over silica gel (eluent: $CH_2Cl_2/CH_3OH$ 95/5). The pure fractions were collected and the solvent was evaporated, yielding 1.5 g (55%) of ethyl 4-[[3,4-dihydrobenzofuro[3,2-c]pyridin-2(1H)-yl]methyl]-1-piperidinecarboxylate (interm. 19).

The following intermediates in tables 1 and 2 were prepared analogous to one of the above examples.

TABLE 1

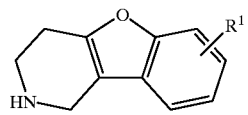

| Interm. No. | Ex. No. | $R^1$ | Physical data |
|---|---|---|---|
| 1 | A1 | H | HCl (1:1) |
| 2 | A2 | 8-F | mp. >300° C.; HCl (1:1) |
| 3 | A2 | 8-$CH_3$ | HCl (1:1) |
| 4 | A3a | 6-$NO_2$ | — |
| 5 | A3a | 6-Cl | — |
| 6 | A3a | 8-Cl | — |

TABLE 2

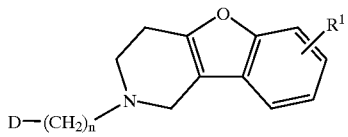

| Interm. No. | Ex. No. | $R^1$ | m | D |
|---|---|---|---|---|
| 7 | A3b | 6-$NH_2$ | 1 | H |
| 8 | A3c | 6-Cl | 1 | H |
| 9 | A3c | 8-Cl | 1 | H |
| 10 | A4a | H | 1 | CN |
| 11 | A4a | H | 3 | CN |
| 12 | A4b | H | 2 | $NH_2$ |
| 13 | A4b | H | 4 | $NH_2$ |
| 14 | A4b | H | 3 | $NH_2$ |
| 15 | A5a | H | 5 | $C_2H_5O-C(=O)-NH-$ |
| 16 | A5b | H | 5 | $NH_2$ |

B. Preparaton of the Final Compounds

EXAMPLE B1 a) A mixture of 3-(2-chloroethyl)-2-methyl-4H-pyrido[1,2-a]pyrimidin-4-one mol), prepared according to the procedures described in EP 0,070,053, free intermediate (1) (0.0040 mol), $Na_2CO_3$ (0.008 mol) and potassium iodide (0.0040 mol) in 4-methyl-2-pentanone (8 ml) was stirred and refluxed overnight. The reaction mixture was cooled. A 50% aqueous NaCl solution and $CH_2Cl_2$ were added. The phases were separated. The aqueous layer was extracted twice with $CH_2Cl_2$. The combined organic layers were dried, filtered and the solvent evaporated. The residue was purified by flash column chromatography over silica gel (eluent: $C_2H_5OH/CH_2Cl_2$ 5/95). The desired fractions were collected and the solvent was evaporated. The residue was triturated and sonicated under DIPE, then filtered off and dried, yielding 0.9 g (63%) 3-[2-[3,4-dihydrobenzofuro[3,2-c]pyridin-2(1H)-yl]ethyl]-2-methyl-4H-pyrido[1,2-a]pyrimidin-4-one (compound 3; mp. 186.2° C.).

b) 6-[[3,4-dihydrobenzofuro[3,2-c]pyridin-2(1H)-yl]ethyl]-3,7-dimethyl-5H-thiazolo-[3,2-a]pyrimidin-5-one (compound 5) was prepared analogous to the procedure described in example B1a but potassium iodide was not added to the reaction mixture.

c) A mixture of intermediate (1) (0.015 mol) and triethylamine (4 g) in 4-methyl-2-pentanone (150 ml) was stirred for 5 minutes. 9-Methoxy-2-methyl-3-[2-[(methylsulfonyl)oxy]ethyl]-4H-pyrido[1,2-a]pyrimidin-4-one (0.015 mol), prepared as described in WO95/14691, was added and the resulting reaction mixture was stirred and refluxed for 6 hours. The mixture was filtered warm and the filtrate was stirred in water (100 ml). The organic layer was separated, dried, filtered, and the solvent was evaporated. The residue was crystallized from DIPE and a small amount of $CH_3CN$. The product was filtered off and dried. This fraction was purified by column chromatography over silica gel (eluent: $CH_2Cl_2/C_2H_5OH$ 92/8). The pure fractions were collected and the solvent was evaporated. The residue was crystallized from DIPE. The precipitate was filtered off and dried, yielding 0.6 g 3-[2-[3,4-dihydrobenzofuro[3,2-c]-pyridin-2 (1H)-yl]ethyl]-9-methoxy-2-methyl-4H-pyrido[1,2-a] pyrimidin-4-one (compound 65; m.p. 151° C.).

EXAMPLE B2

A mixture of intermediate (12) (0.0116 mol), 2-chlorobenzothiazole (0.0118 mol) and $NaHCO_3$ (2 g) in 2-ethoxyethanol (45 ml) was stirred and refluxed for 2 hours. The reaction mixture was cooled and water (45 ml) was added while stirring. The solid was filtered off by suction, washed with water, stirred in DIPE, filtered off and dried. This fraction was dissolved in a small amount of methanol and converted into the (E)-2-butenedioic acid salt (1: 1), while stirring and heating. The mixture was allowed to cool to room temperature with stirring, and the resulting precipitate was filtered off and dried, yielding 3.4 g (63%) N-2-benzothiazole-3,4-dihydrobenzofuro[3,2-c]pyridin-2(1H)-ethanamine (E)-2-butenedioate (1:1) (compound 51; mp 210° C.).

EXAMPLE B3

Potassium hydroxide (0.088 mol) was added to a hot solution of intermediate (19) (0.0044 mol) in 2-propanol (50 ml) and the resulting reaction mixture was stirred and refluxed for 16 hours. The solvent was evaporated. The residue was partitioned between water and $CH_2Cl_2$. The layers were separated. The aqueous phase was extracted three times with $CH_2Cl_2$. The combined organics were dried, filtered and the solvent removed. The residue was purified by flash column chromatography over silica gel (eluent: $CH_2Cl_2/(CH_3OH/NH_3)$ 95/5). The desired fractions were collected and the solvent was evaporated. The residue was dissolved in CHCl₃ (15 ml). Triethylamine (0.726 g) was added. 4-Methylbenzoyl chloride (0.0075 mol) was added and the reaction mixture was stirred for one hour. A 50% aqueous NaOH solution was added. The layers were separated. The aqueous layer was extracted twice with $CH_2Cl_2$. The combined organic layers were dried, filtered and the solvent evaporated. The residue was purified by flash column chromatography over silica gel (eluent: $CH_2Cl_2$/$C_2H_5OH$ 97/3). The pure fractions were collected and the solvent was evaporated. The residue was dried, yielding 1.1 g (64%) 4-[(3,4-dihydrobenzofuro[3,2-c]pyridin-2(1H)-yl)methyl]-1-(4-methylbenzoyl)piperidine (compound 58; mp. 140.3° C.).

EXAMPLE B4

Compound (3) (0.0083 mol) was dissolved in refluxing 2-propanol (80 ml). A mixture of HCl and 2-propanol was added dropwise to the stirring, warm solution, until it became acidic. The desired compound was allowed to crystallize out. The precipitate was filtered off and dried, yielding 3.2 g 3-[2-(3,4-dihydrobenzofuro[3,2-c]pyridin-2(1H)-yl)ethyl]-2-methyl-4H-pyrido[1,2-a]pyrimidin-4-one dihydrochloride (compound 43).

The following compounds in tables 3 and 4 were prepared analogous to one of the above examples.

TABLE 3

| Co. No. | Ex. No. | $R^{1a}$ | $R^{1b}$ | $R^2$ | —$R^3$—$R^4$— | m | Physical data |
|---|---|---|---|---|---|---|---|
| 1 | B1a | H | H | $CH_3$ | —S—CH=CH— | 2 | mp. 166.5° C. |
| 2 | B1a | H | H | $CH_3$ | —$(CH_2)_4$— | 2 | mp. 218.1° C.; fumaric acid (1:1) |
| 3 | B1a | H | H | $CH_3$ | —CH=CH—CH=CH— | 2 | mp. 186.2° C. |
| 4 | B1a | H | H | $CH_3$ | —CH=C($CH_3$)—O— | 2 | mp. 215.7° C.; fumaric acid (2:1) |
| 5 | B1b | H | H | $CH_3$ | —S—CH=C($CH_3$)— | 2 | — |
| 6 | B1b | H | H | $CH_3$ | —S—$(CH_2)_2$— | 2 | — |
| 7 | B1a | H | H | $CH_3$ | —S—$(CH_2)_3$— | 2 | — |
| 8 | B1a | H | H | $CH_3$ | —N($CH_3$)—C($CH_3$)=CH— | 2 | — |
| 9 | B1a | H | H | $CH_3$ | —CH=CH—CH=CH— | 3 | — |
| 10 | B1a | H | H | phenyl | —$(CH_2)_4$— | 2 | — |
| 11 | B1a | H | H | $CH_3$ | —C[=CH—(4F—$C_6H_5$)]—$(CH_2)_3$— | 2 | (E) |
| 12 | B1a | H | H | $CH_3$ | —C[—$CH_2$—(4F—$C_6H_5$)]—$(CH_2)_3$— | 2 | — |
| 13 | B1a | H | H | $CH_3$ | —CH($CH_3$)—$(CH_2)_3$— | 2 | — |
| 14 | B1a | H | H | benzyl | —CH=CH—CH=CH— | 2 | — |
| 15 | B1a | H | H | $CH_3$ | —S—CH=CH— | 3 | — |
| 16 | B1a | 8-F | H | $CH_3$ | —S—CH=CH— | 2 | mp. 179.7° C. |
| 17 | B1a | 8-F | H | $CH_3$ | —CH=CH—CH=CH— | 2 | mp. 203.8° C. |
| 18 | B1a | 8-F | H | $CH_3$ | —$(CH_2)_4$— | 2 | mp. 133.4° C. |
| 19 | B1a | 8-$CH_3$ | H | $CH_3$ | —S—CH=CH— | 2 | — |
| 20 | B1a | 8-$CH_3$ | H | $CH_3$ | —CH=CH—CH=CH— | 2 | — |
| 21 | B1a | 8-$NO_2$ | H | $CH_3$ | —CH=CH—CH=CH— | 2 | — |
| 22 | B1a | 6-$NO_2$ | H | $CH_3$ | —CH=CH—CH=CH— | 2 | — |
| 23 | B1a | 6-Cl | H | $CH_3$ | —CH=CH—CH=CH— | 2 | — |
| 24 | B1a | 8-Cl | H | $CH_3$ | —CH=CH—CH=CH— | 2 | — |
| 25 | B1a | H | H | $CH_3$ | —CH($CH_3$)—$(CH_2)_3$— | 2 | fumaric acid (1:1) |
| 26 | B1b | H | H | $CH_3$ | —CH=CH—CH=CH— | 3 | fumaric acid (1:1) |
| 27 | B1a | H | H | $CH_3$ | —S—CH=CH— | 3 | fumaric acid (1:1) |
| 28 | B1b | H | H | $CH_3$ | —S—$(CH_2)_3$— | 2 | fumaric acid (1:1) |
| 29 | B1a | H | H | benzyl | —CH=CH—CH=CH— | 2 | fumaric acid (1:1) |
| 30 | B1b | H | H | $CH_3$ | —N($CH_3$)—C($CH_3$)=CH— | 2 | fumaric acid (1:1) |
| 31 | B1a | H | H | $CH_3$ | —CH=CH—C(Br)=CH— | 2 | mp. 216° C. |
| 32 | B1a | H | H | $CH_3$ | —CH=CH—C(Cl)=CH— | 2 | mp. 211° C. |
| 33 | B1a | H | H | $CH_3$ | —C($CH_3$)=CH—CH=CH— | 2 | fumaric acid (1:1) |
| 34 | B1a | H | H | $CH_3$ | —CH=CH—C($CH_3$)=CH— | 2 | — |
| 35 | B1b | H | H | $CH_3$ | —C(OH)=CH—CH=CH— | 2 | mp. 200° C. |
| 36 | B1a | H | H | $CH_3$ | —CH=C($CH_3$)—CH=CH— | 2 | — |
| 37 | B1a | H | H | $CH_3$ | —CH=C($CH_3$)—CH=C($CH_3$)— | 2 | fumaric acid (1:1) |
| 38 | B1b | H | H | $CH_3$ | —C(Cl)=CH—C($CF_3$)=CH— | 2 | mp. 205° C. |
| 39 | B1a | H | H | $CH_3$ | —CH=CH—CH=C($CH_3$)— | 2 | — |
| 40 | B1a | H | H | $CH_3$ | —C(Cl)=CH—C(Cl)=CH— | 2 | mp. 215° C. |
| 41 | B1a | H | H | $CH_3$ | —C($NH_2$)=CH—CH=CH— | 2 | — |
| 42 | B1b | H | H | $CH_3$ | —CH=CH—C(I)=CH— | 2 | mp. 210° C. |
| 43 | B4 | H | H | $CH_3$ | —CH=CH—CH=CH— | 2 | HCl (1:2) |
| 44 | B4 | H | H | $CH_3$ | —CH=CH—CH=CH— | 2 | fumaric acid (2:1) |
| 45 | B4 | H | H | $CH_3$ | —CH=CH—CH=CH— | 2 | citric acid (1:1) |

TABLE 3-continued

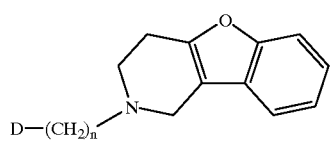

| Co. No. | Ex. No. | R¹ᵃ | R¹ᵇ | R² | —R³—R⁴— | m | Physical data |
|---|---|---|---|---|---|---|---|
| 46 | B4 | H | H | CH₃ | —CH=CH—CH=CH— | 2 | butenedioate (1:1) |
| 47 | B4 | H | H | CH₃ | —CH=CH—CH=CH— | 2 | maleic acid (1:1) |
| 65 | B1c | H | H | CH₃ | —C(OCH₃)=CH—CH=CH— | 2 | mp. 151° C. |
| 66 | B4 | H | H | CH₃ | —CH=CH—CH=CH— | 2 | malic acid |
| 67 | B1a | 6-OCH₃ | 7-OCH₃ | CH | —CH=CH—CH=CH— | 2 | — |

TABLE 4

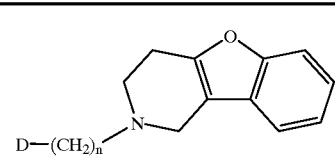

| Co. No. | Ex. No. | n | D- | Physical data |
|---|---|---|---|---|
| 48 | B2 | 5 | (2-benzothiazolyl)-NH— | mp. 207° C.; fumaric acid (1:1) |
| 49 | B2 | 3 | (2-benzothiazolyl)-NH— | mp. 150° C. |
| 50 | B2 | 4 | (2-benzothiazolyl)-NH— | mp. 124° C. |
| 51 | B2 | 2 | (2-benzothiazolyl)-NH— | mp. 210° C. fumaric acid (1:1) |
| 52 | B1a | 2 | 2-oxo-2,3-dihydro-1H-benzimidazolyl | fumaric acid (1:1) |
| 53 | B1a | 3 | 2-oxo-2,3-dihydro-1H-benzimidazolyl | — |
| 54 | B1a | 2 | (1,3-dimethyl-2-oxo-2,3-dihydro-1H-benzimidazolyl structure) | — |
| 55 | B1a | 2 | (2-methylthio-3,5-dimethyl-6-oxo-pyrimidinyl structure) | fumaric acid (1:1) |
| 56 | B1a | 2 | (2-methylthio-1,5-dimethyl-6-oxo-pyrimidinyl structure) | — |
| 57 | B3 | 1 | 1-[(4-methylphenyl)carbonyl]-3-piperidinyl | mp. 201.9° C.; HCl (1:1) |
| 58 | B3 | 1 | 1-[(4-methylphenyl)carbonyl]-4-piperidinyl | mp. 140.3° C. |

TABLE 4-continued

| Co. No. | Ex. No. | n | D- | Physical data |
|---|---|---|---|---|
| 59 | B1a | 2 | (caffeine structure) | fumaric acid (1:1) |
| 60 | B1a | 3 | 2(3H)benzoxazolone-3-yl | — |
| 61 | B1a | 2 | (1-methylbenzimidazolyl structure) | — |
| 62 | B1a | 2 | (benzothiazolo-pyrimidinone structure) | — |
| 63 | B1a | 4 | (3-methyl-2,4(1H,3H)-quinazolinedione structure) | — |

TABLE 4-continued

| Co. No. | Ex. No. | n | D- | Physical data |
|---|---|---|---|---|
| 64 | B1a | 3 | (quinazoline-2,4-dione with N-methyl) | — |

Structure shown: D—(CH$_2$)$_n$— attached to a tetrahydropyrido-benzofuran system.

Table 5 lists both the experimental (column heading "Exp") and theoretical (column heading "The") elemental analysis values for carbon, hydrogen and nitrogen for the compounds as prepared in the experimental part hereinabove.

compound are added to the incubation mixture containing the receptor preparation and the radioligand. Binding of the radioligand will be inhibited by the test compound in proportion to its binding affinity and its concentration.

The radioligand used for $\alpha_{2A}$ receptor binding is $^3$H-rauwolscine and the receptor preparation used is the Chinese Hamster Ovary (CHO) cell expressing cloned human $\alpha_{2A}$ receptors. The compounds with number 1 to 8, 10, 13 to 15, 17, 18, 23 to 25, 27 to 31, 33, 34, 36 to 38, 48, 49, 52, 53, 55, 56, 60, 62, 63, 65 and 66 produced an inhibition of more than 50% at a test concentration of $10^{-8}$ M or less; the compounds with number 9, 11, 12, 16, 19, 20, 22, 26, 35, 41, 44, 51, 57, 58, 59 and 64 produced an inhibition of more than 50% at a test concentration ranging between $10^{-6}$ M and $10^{-8}$ M, and the other compounds produced an inhibition of less than 50% at a test concentration of $10^{-6}$ M.

The radioligand used for $\alpha_{2B}$ receptor binding is $^3$H-rauwolscine and the receptor preparation used is the CHO cell expressing cloned human $\alpha_{2B}$ receptors. The compounds with number 1 to 8, 10, 13 to 15, 23, 25 to 28, 30, 31, 33, 34, 38 to 40, 48 to 50, 52, 53, 55, 56, 62, 63 and 66 produced an inhibition of more than 50% at a test concentration of $10^{-8}$ M or less; the compounds with number 9, 11, 12, 16 to 19, 24, 29, 35 to 37, 41, 44, 49, 51, 54,

TABLE 5

| Co. no. | C The | C Exp | H The | H Exp | N The | N Exp | Co. no. | C The | C Exp | H The | H Exp | N The | N Exp |
|---|---|---|---|---|---|---|---|---|---|---|---|---|---|
| 1 | 65.7 | 65.3 | 5.2 | 5.2 | 11.5 | 11.3 | 39 | 74.0 | 73.5 | 6.2 | 6.1 | 11.3 | 11.1 |
| 2 | 65.1 | 64.7 | 6.1 | 6.0 | 8.8 | 8.7 | 40 | 61.7 | 61.1 | 4.5 | 4.4 | 9.8 | 9.6 |
| 3 | 73.5 | 72.5 | 5.9 | 5.9 | 11.7 | 11.4 | 41 | 70.6 | 43.6 | 5.9 | 3.4 | 15.0 | 29.4 |
| 4 | 65.6 | 65.5 | 5.5 | 5.6 | 10.0 | 10.0 | 42 | 54.5 | 53.6 | 4.2 | 4.0 | 8.7 | 8.2 |
| 5 | 66.5 | 66.2 | 5.6 | 5.3 | 11.1 | 11.2 | 43 | 61.1 | 60.8 | 5.4 | 5.3 | 9.7 | 9.6 |
| 6 | 65.4 | 65.4 | 5.8 | 5.7 | 11.4 | 11.5 | 44 | 69.1 | 68.8 | 5.6 | 5.6 | 10.1 | 10.0 |
| 10 | 76.9 | 76.1 | 5.5 | 5.2 | 10.0 | 9.8 | 45 | 61.0 | 60.8 | 5.3 | 5.3 | 7.6 | 7.4 |
| 21 | 65.3 | 64.1 | 5.0 | 4.6 | 13.9 | 13.3 | 46 | 65.4 | 65.1 | 5.7 | 5.8 | 8.8 | 8.7 |
| 22 | 65.3 | 64.8 | 5.0 | 4.8 | 13.9 | 13.5 | 47 | 65.7 | 65.7 | 5.3 | 5.2 | 8.8 | 8.6 |
| 23 | 67.1 | 66.0 | 5.1 | 5.0 | 10.7 | 10.5 | 65 | 70.9 | 70.6 | 6.0 | 5.8 | 10.8 | 10.9 |
| 25 | 65.7 | 65.5 | 6.3 | 6.4 | 8.5 | 8.4 | 66 | 63.3 | 61.2 | 5.5 | 5.4 | 8.5 | 7.9 |
| 27 | 60.6 | 60.5 | 5.1 | 5.0 | 8.5 | 8.1 | 48 | 63.9 | 63.7 | 5.8 | 5.7 | 8.3 | 8.4 |
| 28 | 60.4 | 60.0 | 5.5 | 5.5 | 8.5 | 8.3 | 49 | 69.4 | 68.7 | 5.8 | 5.7 | 11.6 | 11.4 |
| 29 | 69.7 | 69.5 | 5.3 | 5.3 | 7.6 | 7.5 | 51 | 61.9 | 62.3 | 5.0 | 5.0 | 9.0 | 8.9 |
| 30 | 63.4 | 63.2 | 5.7 | 6.0 | 11.4 | 11.0 | 52 | 64.8 | 64.5 | 5.4 | 5.4 | 9.1 | 8.8 |
| 31 | 60.3 | 59.8 | 4.6 | 4.6 | 9.6 | 9.5 | 55 | 59.4 | 59.3 | 5.6 | 5.6 | 8.7 | 8.6 |
| 32 | 67.1 | 65.7 | 5.1 | 5.0 | 10.7 | 10.4 | 57 | 70.7 | 70.8 | 6.9 | 7.0 | 6.6 | 6.6 |
| 33 | 66.3 | 66.4 | 5.6 | 5.5 | 8.6 | 8.5 | 58 | 77.3 | 76.7 | 7.3 | 7.2 | 7.2 | 7.0 |
| 34 | 74.0 | 72.6 | 6.2 | 6.3 | 11.3 | 11.3 | 59 | 58.2 | 57.5 | 5.1 | 4.7 | 14.1 | 14.0 |
| 35 | 70.4 | 69.6 | 5.6 | 5.7 | 11.2 | 11.0 | 60 | 72.4 | 72.2 | 5.8 | 5.7 | 8.0 | 7.8 |
| 38 | 59.8 | 59.8 | 4.2 | 4.1 | 9.1 | 9.0 | 62 | 69.4 | 69.4 | 5.1 | 4.9 | 10.1 | 10.3 |

C. Pharmacological examples

EXAMPLE C.1

In Vitro Binding Affinity for $\alpha_2$ Receptors

The interaction of the compounds of formula (I) with $\alpha_2$ receptors was assessed in in vitro radioligand binding experiments.

In general, a low concentration of a radioligand with a high binding affinity for a particular receptor is incubated with a sample of a tissue preparation enriched in a particular receptor or with a preparation of cells expressing cloned human receptors in a buffered medium. During the incubation, the radioligand binds to the receptor. When equilibrium of binding is reached, the receptor bound radioactivity is separated from the non-bound radioactivity, and the receptor bound activity is counted. The interaction of the test compounds with the receptor is assessed in competition binding experiments. Various concentrations of the test 57 to 61, 64 and 65 produced an inhibition of more than 50% at a test concentration ranging between $10^{-6}$ M and $10^{-8}$ M, and the other compounds produced an inhibition of less than 50% at a test concentration of 10-6 M. The radioligand used for $\alpha_{2C}$ receptor binding affinity is $^3$H-rauwolscine and the receptor preparation used is the CHO cell expressing cloned human $\alpha_{2C}$ receptors. The compounds with number 1 to 6, 8, 10, 13, 14, 23, 25, 27 to 31, 33, 34, 36 to 40, 48, 50, 52, 53, 55, 58, 62, 63, 65 and 66 produced an inhibition of more than 50% at a test concentration of $10^{-8}$ M or less; the compounds with number 7, 9, 11, 12, 15 to 19, 22, 24, 26, 35, 41, 44, 49, 51, 56, 57, 59 to 61 and 64 produced an inhibition of more than 50% at a test concentration ranging between $10^{-6}$ M and $10^{-8}$ M, and the other compounds produced an inhibition of less than 50% at a test concentration of $10^{-6}$ M.

EXAMPLE C.2
Xylazine-induced Loss of Righting Reflex in Rats

This test is based upon the fact that centrally acting $\alpha_2$-adrenoceptor antagonists reverse the loss of righting reflex induced by an intravenous injection of the $\alpha_2$ agonist xylazine. One hour before injection of xylazine (15 mg/kg, i.v.), male rats (200–250 g) were pretreated with a test compound (er os (p.o.) or subcutaneously (s.c.)) or solvent. In the solvent-treated rats, xylazine-induced loss of the righting reflex was recorded up to 120 minutes after injection. The criterion used for an active test compound was the absence of loss of righting reflex. The lowest active dose (LAD) of the test compounds for xylazine antagonism is defined as the lowest tested dose at which at least 66% of the tested animals showed no loss of righting reflex. Table 6 lists the test results for the present compounds.

TABLE 6

| Comp. No. | Administration route | LAD in mg/kg | Comp. No. | Administration route | LAD in mg/kg |
| --- | --- | --- | --- | --- | --- |
| 1 | s.c. | 0.63 | 32 | s.c. | 0.04 |
| 2 | p.o. | 1.25 | 33 | s.c. | 10.00 |
| 3 | s.c. | 0.08 | 34 | s.c. | 0.16 |
| 3 | p.o. | 0.31 | 35 | s.c. | 10.00 |
| 4 | p.o. | 1.25 | 36 | s.c. | 0.63 |
| 5 | s.c. | 0.63 | 37 | s.c. | 10.00 |
| 6 | s.c. | 0.63 | 38 | p.o. | 10.00 |
| 10 | s.c. | 10.00 | 39 | s.c. | 0.63 |
| 16 | p.o. | 10.00 | 40 | p.o. | 10.00 |
| 17 | s.c. | 10.00 | 48 | s.c. | 10.00 |
| 17 | p.o. | 10.00 | 49 | s.c. | 10.00 |
| 18 | s.c. | 10.00 | 50 | s.c. | 10.00 |
| 19 | s.c. | 10.00 | 51 | s.c. | 10.00 |
| 22 | p.o. | 10.00 | 52 | s.c. | 10.00 |
| 23 | s.c. | 2.50 | 55 | p.o. | 10.00 |
| 24 | p.o. | 10.00 | 57 | p.o. | 10.00 |
| 25 | p.o. | 10.00 | 58 | p.o. | 2.50 |
| 26 | s.c. | 10.00 | 59 | s.c. | 10.00 |
| 27 | s.c. | 10.00 | 60 | p.o. | 10.00 |
| 28 | s.c. | 0.63 | 62 | p.o. | 10.00 |
| 29 | s.c. | 10.00 | 65 | s.c. | 0.63 |
| 30 | s.c. | 2.50 | 66 | s.c. | 0.63 |
| 31 | s.c. | 0.16 | | | |

D. Compositition Examples

"Active ingredient" (A.I.) as used throughout these examples relates to a compound of formula (I), a pharmaceutically acceptable addition salt or a stereochemically isomeric form thereof.

EXAMPLE 1
Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each conprising 20 mg of the A.I.

EXAMPLE D.2
Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

EXAMPLE D.3
Oral Solution

9 Grams of methyl 4-hydroxybenzoate and 1 gram of propyl 4-hydroxybenzoate were dissolved in 4 l of boiling purified water. In 3 l of this solution were dissolved first 10 grams of 2,3-dihydroxybutanedioic acid and thereafter 20 grams of the A.I. The latter solution was combined with the remaining part of the former solution and 12 l 1,2,3-propanetriol and 3 l of sorbitol 70% solution were added thereto. 40 Grams of sodium saccharin were dissolved in 0.5 l of water and 2 ml of raspberry and 2 ml of gooseberry essence were added. The latter solution was combined with the former, water was added q.s. to a volume of 20 l providing an oral solution comprising 5 mg of the active ingredient per teaspoonful (5 ml). The resulting solution was filled in suitable containers.

EXAMPLE D.4
Injectable Solution 1.8 Grams methyl 4-hydroxybenzoate and 0.2 grams propyl 4-hydroxybenzoate were dissolved in about 0.5 l of boiling water for injection. After cooling to about 50° C. there were added while stirring 4 grams lactic acid, 0.05 grams propylene glycol and 4 grams of the A.I. The solution was cooled to room temperature and supplemented with water for injection q.s. ad 1 l, giving a solution comprising 4 mg/ml of A.I. The solution was sterilized by filtration and filled in sterile containers.

What is claimed is:

1. A compound of formula

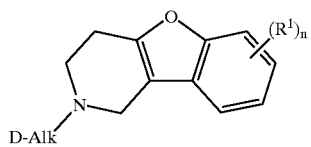

(I)

a pharmaceutically acceptable addition salt or a stereochemically isomeric form thereof, wherein:
each $R^1$ is independently hydrogen, halogen, $C_{1-6}$alkyl, nitro, hydroxy or $C_{1-4}$alkyloxy;
Alk is $C_{1-6}$alkanediyl;
n is 1 or 2;

D is a radical of formula (a)
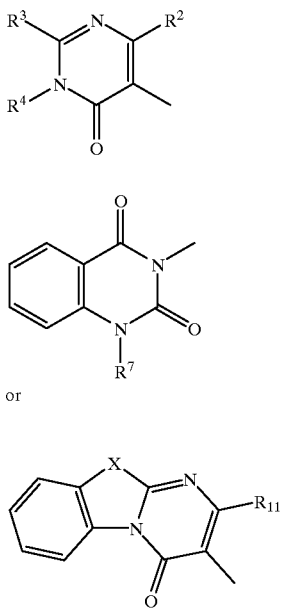

(c)

or (g)
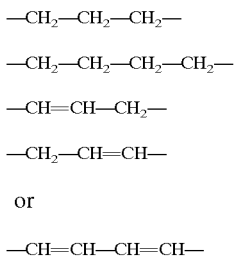

wherein
each X independently represents O, S or NR$^{12}$;
R$^2$ is hydrogen, C$_{1-6}$alkyl, aryl or arylC$_{1-6}$alkyl;
R$^3$ is hydrogen, C$_{1-6}$alkyl, C$_{1-6}$alkyloxy, C$_{1-6}$alkylthio, amino or mono- or di(C$_{1-6}$alkyl)amino;
R$^4$, R$^7$, R$^{11}$ and R$^{12}$ each independently are hydrogen or C$_{1-6}$alkyl; or
R$^3$ and R$^4$ taken together may form a bivalent radical —R$^3$—R$^4$— of formula —CH$_2$—CH$_2$—CH$_2$— (a-1);

—CH$_2$—CH$_2$—CH$_2$—CH$_2$— (a-2);

—CH=CH—CH$_2$— (a-3);

—CH$_2$—CH=CH— (a-4);

or

—CH=CH—CH=CH— (a-5);

wherein one or two hydrogen atoms of said radicals (a-1) to (a-5) each independently may be replaced by halo, C$_{1-6}$alkyl, arylC$_{1-6}$alkyl, trifluoromethyl, amino, hydroxy, C$_{1-6}$alkyloxy or C$_{1-10}$alkylcarbonyloxy; or where possible, two geminal hydrogen atoms may be replaced by C$_{1-6}$alkylidene or arylC$_{1-6}$alkylidene; or —R$^3$—R$^4$— may also be —S—CH$_2$—CH$_2$— (a-6);

—S—CH$_2$—CH$_2$—CH$_2$— (a-7);

—S—CH=CH— (a-8);

—NH—CH$_2$—CH$_2$— (a-9);

—NH—CH$_2$—CH$_2$—CH$_2$— (a-10);

—NH—CH=CH— (a-11);

—NH—CH=N— (a-12);

—S—CH=N— (a-13);

or

—CH=CH—O— (a-14);

wherein one or where possible two or three hydrogen atoms in said radicals (a-6) to (a-14) each independently may be replaced by C$_{1-6}$alkyl or aryl; and
aryl is phenyl or phenyl substituted with halo or C$_{1-6}$alkyl.

2. A compound according to claim 1 wherein D is a radical of formula (a) wherein R$^3$ is C$_{1-6}$alkylthio and R$^4$ is C$_{1-6}$alkyl; or wherein R3 and R$^4$ are taken together to form a bivalent radical of formula (a-2) or (a-5) wherein one or two hydrogen atoms of said radicals each independently may be replaced by halo, C$_{1-6}$alkyl, C$_{1-6}$alkyloxy, arylC$_{1-6}$alkyl, trifluoromethyl, amino, hydroxy, or C$_{1-10}$alkylcarbonyloxy; or where possible, two geminal hydrogen atoms may be replaced by C$_{1-6}$alkylidene or arylC$_{1-6}$alkylidene; or a bivalent radical of formula (a-6), (a-7), (a-8), (a-11) or (a-14) wherein one or where possible two or three hydrogen atoms in said radicals each independently may be replaced by C$_{1-6}$alkyl or aryl; or D is a radical of formula (c) wherein R$^7$ is hydrogen; or D is a radical of formula (g) wherein X is S and R$^{11}$ is C$_{1-6}$alkyl.

3. A compound according to claim 1 wherein n is 1 and R$^1$ is hydrogen, chloro, fluoro, methyl or nitro, or wherein n is 2 and R$^1$ is methoxy.

4. A compound according to claim 1 wherein R$^1$ is hydrogen and D is a radical of formula (a) wherein R$^3$ and R$^4$ are taken together to form a bivalent radical of formula (a-2) or (a-5) wherein one or two hydrogen atoms each independently may be replaced by halo, methyl, methoxy, arylmethyl, trifluoromethyl, amino or hydroxy, or wherein two geminal hydrogen atoms are replaced by arylmethylene; or R$^3$ and R$^4$ taken together form a bivalent radical of formula (a-6), (a-7), (a-8), (a-11) or (a-14) wherein one or where possible two or three hydrogen atoms are replaced by methyl.

5. A compound according to claim 1 wherein the compound is
3-[2-[3,4-dihydrobenzofuro[3,2-c]pyridin-2(1H)-yl]ethyl]-2-methyl-4H-pyrido-[1,2-a]pyrimidin-4-one;
6-[[3,4-dihydrobenzofuro[3,2-c]pyridin-2(1H)-yl]ethyl]-7-methyl-5H-thiazolo-[3,2-a]pyrimidin-5-one;
6-[[3,4-dihydrobenzofuro[3,2-c]pyridin-2(1H)-yl]ethyl]-3,7-dimethyl-5H-thiazolo-[3,2-a]pyrimidin-5-one;
3-[2-[3,4-dihydrobenzofuro[3,2-c]pyridin-2(1H)-yl]ethyl]-2,7-dimethyl-4H-pyrido-[1,2-a]pyrimidin-4-one; a pharmaceutically acceptable addition salt or a stereochemically isomeric form thereof.

6. A composition comprising a pharmaceutically acceptable carrier and, as active ingredient, a therapeutically effective amount of a compound as claimed in claim 1.

7. A process for preparing a pharmaceutical composition claim 6 by combining a compound as defined in of claim 1 as the active ingredient in intimitate admixture with a pharmaceutically acceptable carrier.

8. A process for preparing a compound according to claim 1, characterized by,
a) N-alkylating a 1,2,3,4-tetrahydro-benzofurano[3,2-c]pyridine derivative of formula (II) with an alkylating reagent of formula (III)

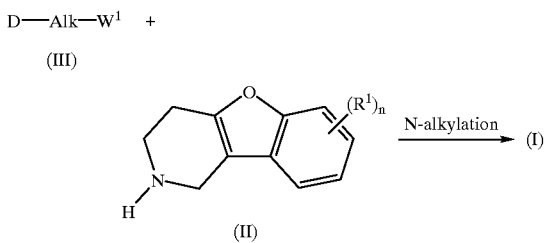

wherein W¹ represents an appropriate reactive leaving group, and D, Alk and R¹ are as defined in claim 1;

d) and if desired, converting compounds of formula (I) into each other following art-known transformations, and further, if desired, converting the compounds of formula (I), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms thereof.

9. A method of treating depression in a warm-blooded animal in need thereof comprising administering to the animal a therapeutically effective amount of the compound of claim 1.

10. A method of treating Parkinson's disease in a warm-blooded animal in need thereof comprising administering to the animal a therapeutically effective amount of the compound of claim 1.

* * * * *